US010417384B2

(12) United States Patent
Lauchard et al.

(10) Patent No.: US 10,417,384 B2
(45) Date of Patent: *Sep. 17, 2019

(54) MEDICAL DEVICE CONNECTION STATION

(71) Applicant: ARES TRADING S.A., Aubonne (CH)

(72) Inventors: Gerhard Lauchard, Siberegg (AT);
Gerhard Walder, Villach (AT);
Alexander Legner, Althofen (AT); Eric
Chanie, Geneva (CH); Georgios
Kouvas, Geneva (CH)

(73) Assignee: ARES TRADING S.A., Aubonne (CH)

( * ) Notice: Subject to any disclaimer, the term of this patent is extended or adjusted under 35 U.S.C. 154(b) by 133 days.

This patent is subject to a terminal disclaimer.

(21) Appl. No.: 15/101,702

(22) PCT Filed: Dec. 4, 2014

(86) PCT No.: PCT/EP2014/076482
§ 371 (c)(1),
(2) Date: Jun. 3, 2016

(87) PCT Pub. No.: WO2015/082578
PCT Pub. Date: Jun. 11, 2015

(65) Prior Publication Data
US 2016/0314262 A1 Oct. 27, 2016

(30) Foreign Application Priority Data

Dec. 5, 2013 (EP) .................................. 13195960
Jan. 13, 2014 (EP) .................................. 14150907
Jan. 13, 2014 (EP) .................................. 14150908

(51) Int. Cl.
*G06F 15/16* (2006.01)
*G06F 19/00* (2018.01)
(Continued)

(52) U.S. Cl.
CPC ........... *G06F 19/3418* (2013.01); *A61M 5/31* (2013.01); *A61M 15/009* (2013.01);
(Continued)

(58) Field of Classification Search
CPC ..... H04L 67/12; H04L 67/42; G06F 19/3462; G06F 19/3456; G06F 19/3418
(Continued)

(56) References Cited

U.S. PATENT DOCUMENTS

2006/0154642 A1 7/2006 Scannell, Jr.
2010/0211005 A1* 8/2010 Edwards ............... A61M 5/002
604/82
2013/0317753 A1* 11/2013 Kamen ............... G06F 19/3418
702/19

FOREIGN PATENT DOCUMENTS

WO 2010056712 A1 5/2010
WO 2013071225 A1 5/2013
WO 2015082578 A1 6/2015

OTHER PUBLICATIONS

PCT/EP2014/076482—International Search Report and Written Opinion, dated May 18, 2015, 24 pages.
* cited by examiner

*Primary Examiner* — Wing F Chan
*Assistant Examiner* — Andrew Woo
(74) *Attorney, Agent, or Firm* — Carter, DeLuca & Farrell LLP

(57) ABSTRACT

A medical device connection station comprising a body having a first portion of a docking interface to dock with a corresponding second portion of a docking interface of a medical device, a control unit controlling a medical device communication interface for communication with a docked medical device and controlling a server communication interface. The control unit is configured acquire medical data from a docked medical device via the medical device communication interface and is further configured to connect with and obtain a data session with the server system via the server communication interface, and to thereby transfer the medical data to the server system. The medical (Continued)

device connection station further comprises a lid connected to the body and movable between a first and second position, wherein in the first position the lid prevents first portion of the docking interface from docking with the second portion of the docking interface of the medical device, and wherein in the second position the first portion of the docking interface is operable to dock with the second portion of the docking interface. The medical device connection station comprises a lid movement sensing unit which is configured to sense movement of the lid between the first position and the second position and to thereby provide a signal to the control unit, the control unit configured to receive the signal to initiate the connection to the server system.

20 Claims, 3 Drawing Sheets

(51) Int. Cl.
*G06F 1/16* (2006.01)
*A61M 5/31* (2006.01)
*A61M 15/00* (2006.01)
*H04L 29/06* (2006.01)
*H04L 29/08* (2006.01)
*G16H 40/63* (2018.01)

(52) U.S. Cl.
CPC ............ *G06F 1/1632* (2013.01); *H04L 67/42* (2013.01); *A61M 2205/3553* (2013.01); *A61M 2205/3569* (2013.01); *A61M 2205/3584* (2013.01); *A61M 2205/502* (2013.01); *A61M 2205/52* (2013.01); *A61M 2230/005* (2013.01); *G06F 19/3456* (2013.01); *G06F 19/3462* (2013.01); *G06F 19/3468* (2013.01); *G16H 40/63* (2018.01); *H04L 67/12* (2013.01); *H04L 67/141* (2013.01)

(58) Field of Classification Search
USPC .................................................. 709/217, 218
See application file for complete search history.

MEDICAL DEVICE CONNECTION STATION

This application is a national stage filing of International Application No. PCT/EP2014/076482, filed Dec. 4, 2014, which claims benefit of priority pursuant to EP 13195960.3, filed Dec. 5, 2013, EP 14150908.3, filed Jan. 13, 2014, and EP 14150907.5, filed on Jan. 13, 2014.

The entire disclosures of the afore-mentioned patent applications are incorporated herein by reference.

TECHNICAL FIELD

The present invention relates to a medical device connection station which is configured to transfer medical data from a medical computer device docked therewith to a remote server system.

BACKGROUND

Increasingly medical computer devices, such as electronically enabled drug delivery devices, are configured to record usage data that relates to the usage of the device. In the example where the medical computer device is a drug delivery device, the usage data may include the: administered dosage regimen, for example, the delivered quantity of a medicament; the associated delivery history; the adherence to a predetermined dosage regimen. An example of such a drug delivery device is provided in WO 2005/077441, WO 2006/085175, WO 2006/085204 and WO 2007/088444, the products pertaining to which are offered by Merck Serono S. A under the RebiSmart™ and Easypod™ trademarks. In an alternate example a drug delivery device may comprise a communications interface for communication with an intermediate medical computer device whereon the usage parameters can be transferred and recorded.

It is desirable to supply the recorded usage data to a server system, such that the data can be permanently recorded on a database of the server system and subsequently analysed by a health care professional if necessary. One such way of supplying the recorded data is to configure the above drug delivery device to be dockable, for data transfer, with a connection station that is in communication with the server system, wherein data exchange between the drug delivery device and server system occurs via the connection station. It is advantageous to provide a connection station with such functionality as opposed to incorporating the functionality in the drug delivery device for reasons of approval by governing bodies in various jurisdictions, for example, the federal food and drug agency (FDA) in the US. Notably, drug delivery device incorporating new functionally may take several years to receive approval, whereas a connection station that works with an approved drug delivery device does not require such approval.

When using a connection station the drug delivery device is docked with the connection station and thereafter and actuator may be depressed to effect initiation of a connection and a subsequent data session between the connection station and server system.

A drawback with such operation of the connection station is that a user may forget to depress the actuator, and thus the medical device is docked with the connection station without the required data session. Moreover, the user may find it difficult to depress the actuator. The aforementioned may be exacerbated by certain medical conditions, such as Multiple Sclerosis, the conditions of which can manifest as visual, motor, and sensory problems as well as cognitive problems.

A further drawback is that, for convenience of use, it is desirable to provide a docking interface between the medical computer device and connection station which operates in a substantially vertical direction. However, with such an arrangement, the docking interface of the connection station is exposed and can thus become contaminated with debris and dust.

A further drawback is that the process of docking the medical computer device with the connection station and the subsequent depression of the actuator and initiation of the connection to the server system delays start-up of the data session.

In certain conventional medical computer devices, a user interface is provided in the form of a display means for display of the medical data and a user input device comprising selection keys for operation of the medical device. To analyse the medical data, a patient using the device takes the device to a health care professional (HCP) who, using the user interface, selects and views the medical data.

Thereafter, the HCP may manually enter the data into a remote server system wherein it is stored for future analysis. A drawback with this system is that the HPC may incorrectly enter some of the medical data into the server system. Moreover, the process of transporting the medical computer device to the HCP for analysis of the medical data is burdensome on the patient as is entry of the medical data into the server system by the HCP.

SUMMARY OF THE INVENTION

An object of the invention is to provide a medical computer device connection station which is convenient and easy to use, particularly for medical patients who suffer from medical conditions with symptoms that can exacerbate the difficulty in using such devices.

It would be advantageous to provide a medical computer device connection station which does not suffer from problems associated with contamination of the docking interface.

It would be advantageous to provide a medical computer device connection station which can connect to a remote server system and start-up a data session conveniently.

It would be advantageous to provide a medical computer device connection station which is economical and easy to manufacture.

It would be advantageous to provide a medical computer device which is operable to conveniently transfer medical data when the medical patient is at various geographical locations remote from the server system.

In particular for patients who as part of their treatment regimen take regular dosages of a medicament, such as Rebif™ for treatment of multiple Sclerosis, such a device would be advantageous as it is necessary for the patient to have drug delivery device in their possession when traveling and a terminal to interface with the server system cannot be guaranteed.

Various objects of the invention are achieved by:
a medical device connection station according to claims 1-14;
a system to transfer medical data from a medical device to a server system according to claims 15-16; and
a method of transferring medical data from a medical device to a server system according to claims 17-20;

Disclosed herein is a medical device connection station comprising a body having a first portion of a docking interface cavity to dock with a corresponding second portion of a docking interface of a medical device, a control unit controlling a medical device communication interface for communication with a docked medical device and controlling a server communication interface. The control unit is configured acquire medical data from a docked medical device via the medical device communication interface and is further configured to connect with and obtain a data session with the server system via the server communication interface, and to thereby transfer the medical data to the server system.

According to a first aspect of the invention, the medical device connection station further comprises a lid connected to the body and movable between a first and second position, wherein in the first position the lid prevents first portion of the docking interface from docking with the second portion of the docking interface of the medical device, and wherein in the second position the first portion of the docking interface is operable to dock with the second portion of the docking interface.

According to a second aspect of the invention the server communication interface comprises a cellular network interface. Advantageously, the medical patient does not need to transport the medical computer device to the medical practitioner for upload of the medical data to the server, rather upload can be performed remotely via the cellular network interface. Moreover, the medical computer device is convenient to use for the HCP since it does not require an intermediate step of the HCP transferring the medical data to the server system. Moreover, the medical computer device can be used in a range of locations since the cellular network interface enables wireless communication over the land areas of each cell. It is advantageous to provide a connection station with such cellular network data transfer capability as opposed to incorporating this capability in a drug delivery device for reasons of approval by governing bodies in various jurisdictions, for example, the federal food and drug agency (FDA) in the US. Notably, drug delivery device incorporating new functionally may take several years to receive approval, whereas a connection station that works with an approved drug delivery device may be easier to obtain approval, if needed.

By using a medical device connection station to transfer the medical data, as opposed to the medical device itself, the medical device can be made disposable and the connection station re-usable, such that relatively expensive components like the communication interfaces and control unit are part of the connection station. Further, a single connection station can be used by a plurality of medical devices, for example at a treatment centre. Yet further, the size and weight of the medical device can be reduced since the aforementioned components are part of the connection station. This is particularly advantageous for medical devices that are carried by the patient as part of day to day use.

A dedicated docking connection station to transfer the medical data as opposed to a more general device, such as a mobile phone, is more convenient to use since the user has merely to dock the medical device with the connection station to ensure transfer of the medical data. Whereas, in the example of a mobile phone, a user would need to install application specific software on the phone, and each time data is transferred, ensure that there is a connection between the medical device and mobile phone. Moreover, a more general device is inherently less secure.

The medical device connection station comprises a lid movement sensing unit which is configured to sense movement of the lid between the first position and the second position and to thereby provide a signal to the control unit, the control unit configured to receive the signal to initiate the connection to the remote server system.

Advantageously, objects of the invention are solved since the lid is convenient to move from the first and second position particularly for medical patients who suffer from medical conditions with symptoms that can exacerbate the difficulty in using such devices. Moreover, the medical device cannot be docked without initiating the connection between the server system and connection station. The lid also prevents contamination of the docking interface with debris and dust. Moreover, the connection station automatically connects to the server system when the lid is moved from the first position to the second position such that when the medical device is subsequently docked, the connection station is ready for data transfer to the server system. In this way the connection station is convenient to operate and the time a user spends operating the connection station can be reduced.

The medical device communication interface may comprise an infra-red interface or other suitable means to receive the medical data. For example, it may comprise a near field communication system.

The lid movement sensing unit may be mechanically actuated comprising a switch unit and an actuation member, the actuation member is configured to engage with and actuate the switch unit as the lid is moved between the first and second position. The switch unit is configured to provide the signal. Alternatively, the lid movement sensing unit may be light intensity or magnetic field actuated.

The lid may be pivotally connected to the body. Alternatively it may be slideably, translateably or flexibly connected to the body. For a pivotally connected lid, the actuation member of the lid movement sensing unit may comprise a cam operable to pivot with the lid to actuate the actuation member, the actuation member being pivotally connected to the body. The lid and body may be configured such that the lid entirely covers the first portion of the docking interface when in the first position. The switch unit may advantageously be mounted on a circuit board arranged adjacent a base of the body distal from the lid. The circuit board may comprise electronic components mounted directly thereon for the various communications functions and control functions, including wireless telecommunications technology (WTT) (e.g a GSM processing chip), a SIM card slot and connector, and infrared or other forms of near field wireless communication with the medical device received in the docking interface cavity. The infrared receiver/transmitter may be positioned on the circuit board just below an infrared transparent window formed in a base wall of the docking cavity.

The server communication interface of the connection station may comprise one or more of: a wireless telecommunications technology (WTT) network interface, in particular a cellular phone network interface, for example, a GSM, 3G or 4G enabled interface with a SIM card; a wired network interface, such as a USB or RJ45 connection; a WLAN network interface, such as a IEEE 802.11 standard. In the example of a WTT network interface the connection station is particularly advantageous since it enables the transfer of the medical data in remote locations or for field nurses or other health care personnel visiting patients.

The connection station may comprise a control module having a cryptographic algorithm to encrypt the received medical data. The control unit may be configured to transfer the encrypted medical data to the server system. In this way confidential medical data can be securely transmitted and stored.

The lid movement sensing unit may be configured to sense movement of the lid from the second position to the first position and to thereby provide a further signal to the control unit, the control unit configured to receive the further signal to terminate the connection to the server system. Alternatively or in addition, control unit may be configured to terminate the connection to the server system after a predetermined period of time. In this way the connection station is energy efficient.

The medical device may be a drug delivery device adapted for subcutaneous delivery of a medicament or may be adapted for delivery by other means, for example, as an aerosol via an inhaler or orally. The medical data may be related to a dosage regimen of the medicament.

Also disclosed herein is a system to transfer medical data from a medical device to a remote server system. The system comprises a medical device, a remote server system and a medical device connection station comprising features of any of the aspects set forth above.

The system may further comprise a remote computer device configured to remotely access the medical data of the server system over the internet so that a healthcare professional (HCP) can review the medical data.

Also disclosed herein is a method of transferring medical data from a medical device to a server system using a medical device connection station comprising features of any of the aspects set forth above.

The method comprises; acquiring medical data on the medical device; connecting the connection station to the server; docking the medical device with the connection station by connecting the first and second portions of the docking interface; transferring the medical data from the medical device to the connection station via a communication interface of the medical device and the medical device communication interface of the connection station; transferring the medical data from the connection station to the server system via the server communication interface of the connection station. According to a first aspect the connection of the connection station to the system is initiated by moving the lid from the first position to the second position.

The method may further comprise encrypting the received medical data on the connection station by means of a cryptographic algorithm of a control module and transferring the encrypted medical data to the server system. The method may further comprise storing the medical data on a database of the server system. The method may further comprise remotely accessing the medical data over the internet using a computer device by a HCP.

Also disclosed herein is a method of assembling a medical device connection station comprising features of any of the aspects set forth above.

The method comprises: mounting the control unit, medical device communication interface, server communication interface on a circuit board; inserting the circuit board with the aforementioned components mounted thereto in a housing of the body wherein the circuit board arranged adjacent a base of the housing; securing the circuit board to the housing using fixing means; movably attaching the lid to the body.

Advantageously, various components may be conveniently mounted directly to the circuit board, including parts of the communication interfaces and the lid movement sensing unit, prior to assembly of the circuit board inside the housing of the body.

The method may further comprise inserting the circuit board in the housing such that an infra-red interface of the medical device communication interface thereon is operable to receive the medical data through a transmissive window in a bottom wall of a docking interface cavity.

The method may further comprise mounting a switch unit on the circuit board prior to insertion of the circuit board, wherein the lid movement sensing unit is mechanically actuated and comprise the switch unit and an actuation member, the actuation member configured to engage with and actuate the switch unit as the lid is moved between the first and second position, the switch unit configured to provide the signal.

The method may further comprise connecting a SIM card to a SIM card connector of the server communication interface that is mounted on the circuit board, wherein the SIM card is connected to the SIM card connector through an aperture in the housing of the body.

Further objects and advantageous features of the invention will be apparent from the claims, from the detailed description, and annexed drawings.

For a better understanding of the invention, and to show how embodiments of the same may be carried into effect, reference will now be made, by way of example, to the accompanying diagrammatic drawings in which:

DETAILED DESCRIPTION OF EXEMPLARY EMBODIMENTS

Figure 1:
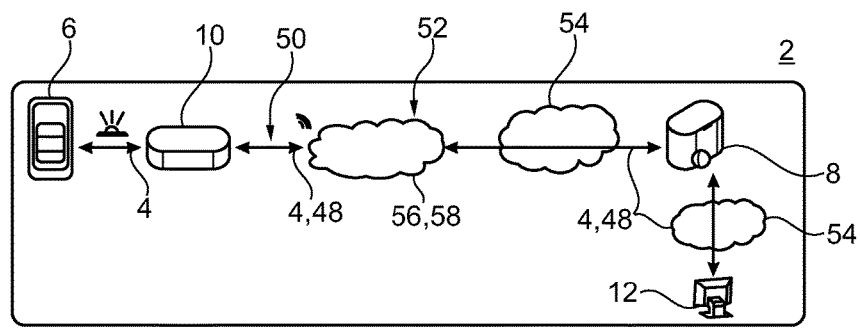
FIG. 1 is an illustrative view of medical system for remotely transferring medical data from a medical device to a server system via a medical device connection station.

FIG. 1 shows a medical system 2 for remotely transferring medical data 4 from a medical device 6 to a remote server system 8 via a medical device connection station 10. The server system may be part of a computerized patient care system or electronic health platform. The medical data 4 can be stored on the server system 8 and remotely accessed by a health care professional (HCP) via a computer device 12, for example over the internet or a LAN.

In an example embodiment the medical device 6 comprises a drug delivery device. The drug delivery device may be adapted for subcutaneous delivery of a medicament or may be adapted for delivery by other means, for example, as an aerosol via an inhaler or orally. The medical device may alternatively comprise an intermediate medical communication device which is operable to receive medical data from the aforementioned drug delivery device.

The medical device 6 comprises a signal processing circuit to acquire, store and transmit the medical data via a connection station communication interface. The signal processing circuit may be idealised as consisting of a: control unit; medical data acquisition unit; and memory unit. The medical data acquisition unit is configured to acquire the medical data, and may for example comprise a sensor for sensing an amount of medicament dispensed, or a communication interface with the relevant hardware. The control unit is configured to process and store the medical data on the memory unit. The memory unit may consist of a non-volatile memory, such as flash memory. The control unit is further configured to transmit the stored medical data to the connection station via the connection station communication interface, which is discussed in more detail in the following.

The medical device 6 may further comprise a user interface, such as a display means for display of the medical data and a user input device comprising selection keys for entry of medical data and/or operation of the medical device. The medical device may further comprise a clock module to synchronise the medical data for providing time and date related medical data.

The medical device 6 comprises a second portion of a docking interface for docking the medical device with the medical device connection station 10.

Herein medical data is defined as any data relation to a treatment regimen including physiological parameters of the patient and data relating to the delivery device or other associated medical device. For example, the medical data may comprise one of more of a list consisting of the following: the medicament which may be identified using an identification code and/or a batch number identification code; the quantity of medicament delivered; a time of delivery of one or more dosage(s); the adherence to a dosage regimen; a medical device identification code, such as a serial number; medical device software identification code; a patient identification code; a physiological parameter of a user, for example body temperature, pulse rate, blood pressure, blood sugar level, galvanic skin surface, a physiologic response to the medicament or other such parameter; medical device performance related parameters, such as an error code, a service device code, a maintenance alarm, a drug level or other such parameter.

Examples of suitable medical devices are provided in WO 2005/077441, WO 2006/085175, WO 2006/085204 and WO 2007/088444 which are incorporated herein by reference. These devices are fully automated and therefore the medical data such as the subcutaneous delivery member speed, penetration depth and dosage, are obtainable by interface of the medical data acquisition unit with the relevant hardware.

The medical device may also be configured to receive data from the connection station, or directly from the server system via the connection station communication interface or other suitable communication interface. The received data may be, for example, a software update, drug information, or a new treatment regimen.

Figures 2A, 2B:
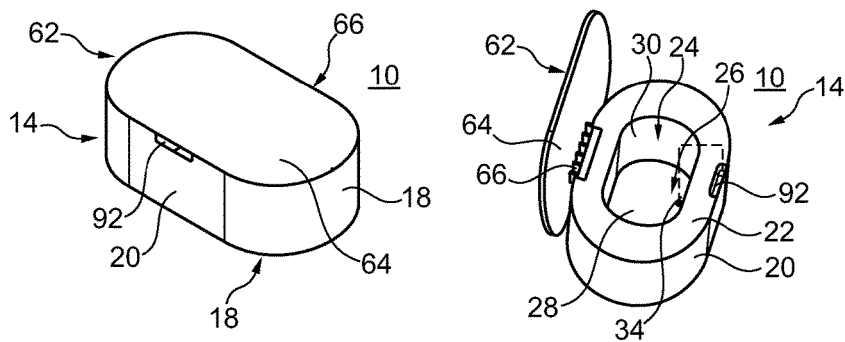
FIG. 2 shows perspective views of various operational states of the connection station of FIG. 1.
Figure 2C:
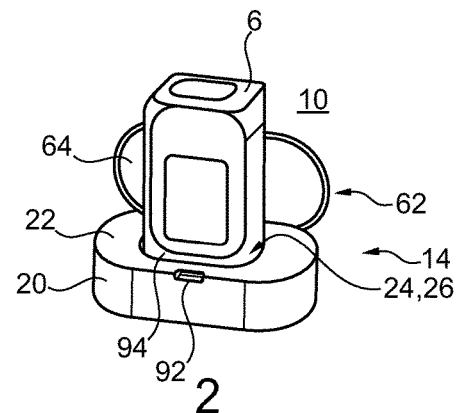
Figure 3:
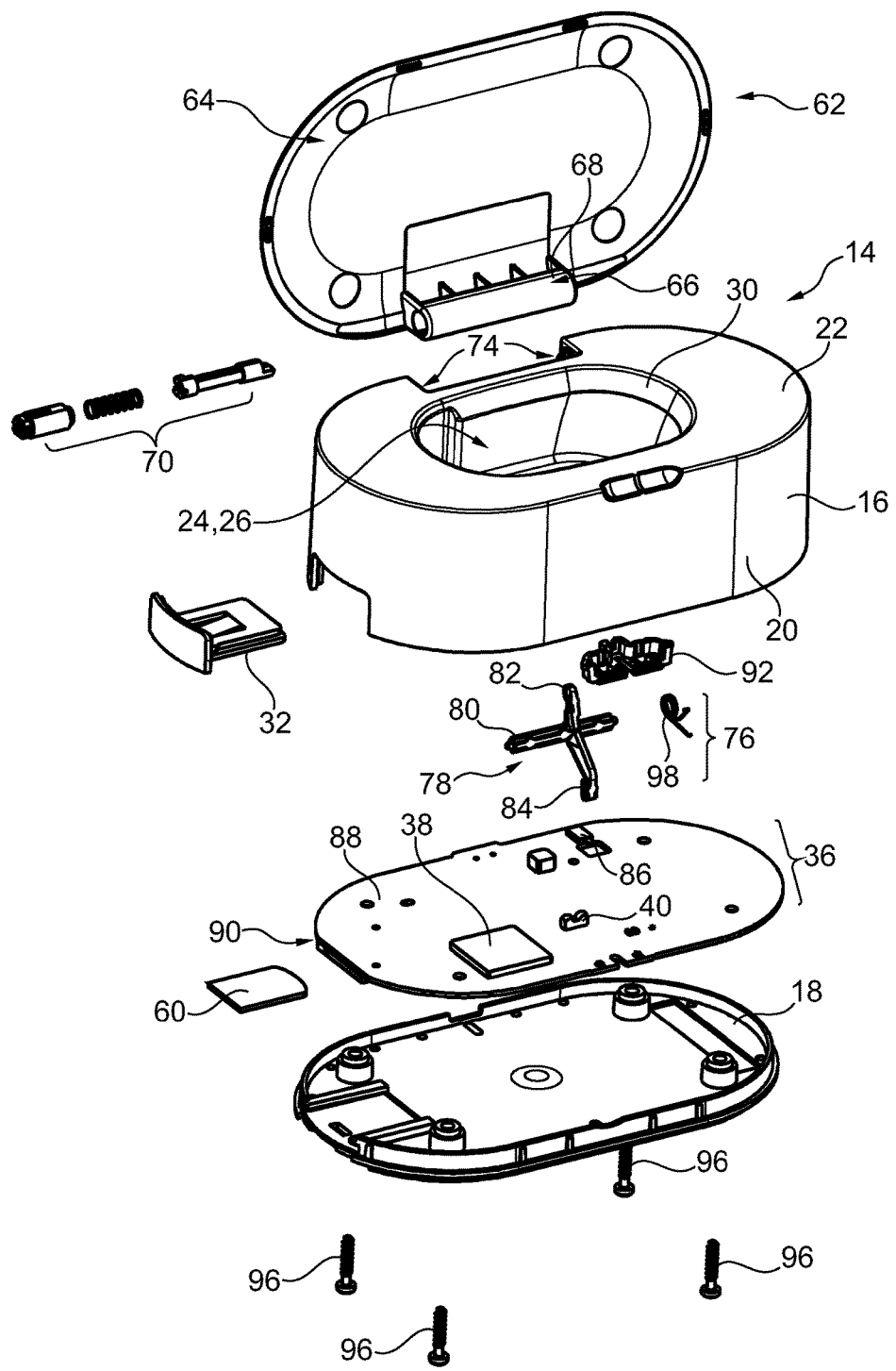
FIG. 3 is an exploded diagram of the connection station of FIG. 1.

Referring now to FIGS. 2-3, the connection station 10 has a body 14 that comprises a housing 16 consisting of a base 18 side wall 20 and top wall 22. The body 14 further comprises a first portion 24 of the docking interface configured to dock with the second portion 94 of the docking interface of the medical device 6.

In the example the first portion 24 of the docking interface is arranged on the top wall 20 of the housing 16 such that the medical device 6 can be conveniently docked in the vertical direction. However, it may be arranged elsewhere on the housing 16, for example on a side wall 18.

The docking interface comprises any arrangement operable to constrain the medical device 6 in 3-dimensions to the body 14. For this purpose the first and second portions of the docking interface may be complementary in shape such that the one of the docking portions fits at least partially within the other of the docking portions. In the example the first portion 24 of the docking interface comprise a docking interface cavity 24 that extends between the top wall 22 and base 18 of the housing 16. The docking interface cavity 24 comprises a bottom wall 28 and side wall 30. The second portion 94 of the docking interface comprises an end of the medical device 6 that is insertable into the docking interface cavity 24. The side wall 30 of the docking interface cavity 24 defines an oval-shaped section with two parallel sides that correspond to the exterior shape of the medical device 6. It will be appreciated that other shapes of medical device and thus docking interfaces can be used.

The docking interface may be shaped such that the medical device can only be docked when orientated correctly. For this purpose the docking interface may have a asymmetric profile. In the example an asymmetric profile is embodied by the curvature of the sides of the medical device 6 being non-symmetric. The second portion 94 and/or first portion 24 of the docking interface may be tapered to facilitate easier docking. In the example an end of the medical device is tapered for this purpose.

The housing 16 of the body 14 may further comprise a subscriber identity module (SIM) card holder 32. In the example shown in FIG. 3, the SIM card holder is arranged on the side wall 20 of the housing 16 and comprises a tray for supporting the SIM card removeably insertable in a slot.

The docking interface cavity 26 may further comprise a transmissive window 34 which in the example is arranged on the bottom wall 28 of the cavity as shown in FIG. 2b. The transmissive window 34 is configured for transfer of the medical data 4 therethrough for an example that comprises an infra-red communication system, which is described in more detail below.

Figure 4:
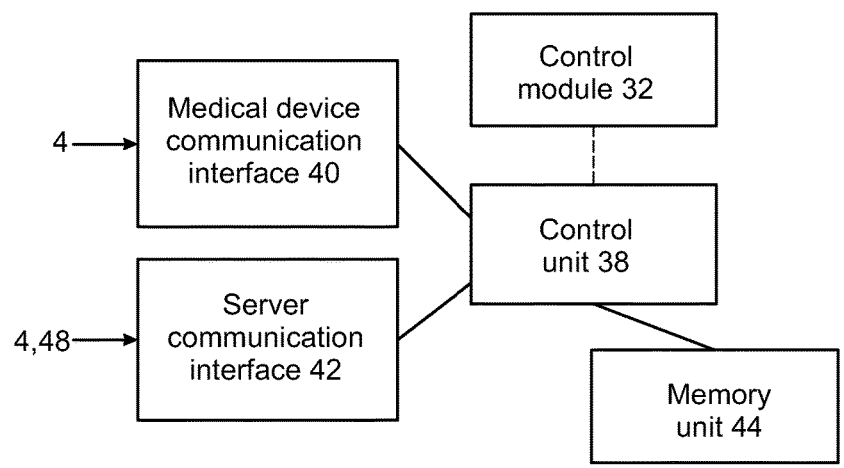
FIG. 4 is a block diagram showing various functional blocks according to an idealisation of the connection station of FIG. 1.

With reference to FIGS. 2b, 3 and 4, the connection station 10 comprises a signal processing circuit 36 to acquire the medical data 4 from the medical device 6 and transmit the medical data to the server system 8. As shown in FIG. 4, the signal processing circuit 36 may be idealised as comprising: a control unit 38; medical device communication interface 40; and server communication interface 42. It may optionally further comprise a memory unit 44 and a control module 46.

The control unit 38 is configured to control the medical device communication interface 40 to receive the medical data 4 from the connection station communication interface of a docked medical device 6. The control unit 38 is further configured to process the medical data 4 and may temporarily store at least part of the data on the memory unit 44. The control unit 38 is further configured to connect with and to obtain a data transfer session with the server system 8 via the server communication interface 42, and to thereby transfer the processed medical data 4 to the server system 8.

Herein the term data transfer session refers to a semi-permanent information exchange between the connection station and server system. For example the session may include a HTTPS (Hyper Text Transfer Protocol Secure) or another suitable session over TCP/IP. In an embodiment where the connection station connects to the server system using wireless telecommunications technology (WTT), The session includes a WTT connection, for instance GPRS or UMTS, between the connection station and the WTT service provider, and a HTTPS or another suitable TCP/IP connection over the internet between the WTT service provider and the server system 8.

The control module 46 comprises software enabling operation of the communication interfaces and processing. The software may for example be stored on the memory unit 44 or on a further memory unit of the control unit 46. The control module 46 may comprise a cryptographic algorithm for encryption of the medical data 4 such that encrypted medical data 48 can be sent from the connection station 10 to the server system 8. The cryptographic algorithm may be a symmetric or asymmetric type. Examples of suitable cryptographic algorithms are: blowfish, AES. An example of an asymmetric cryptographic algorithm is a key pair type. The public key of which may be sent with a certificate to verify the owner of the public key, wherein the certificate is verified by a certification authority.

In an advantageous example, the medical device communication interface 40 of the connection station 10 and the connection station communication interface of the medical device 6 comprise a communication system which is configured to restrict communication only to when the device is docked. For example, the communication system may comprise an infra-red transceiver which is operable to transmit data over short distances and via a line of site. The communication system may alternatively be a near field communication system.

In the example shown in FIGS. 2b and 3 an infra-red transceiver 40 is located proximate the bottom wall 28 of the docking interface cavity 26 of the docking interface, such that it can transmit and receive data through the transmissive window 34. A corresponding infra-red transceiver and transmissive window are arranged on the medical device 6.

The server communication interface 42 of the connection station 10 comprises any suitable means for wireless or wired data transmission. For wired transmission it may comprise a wired interface such as a USB interface or an Ethernet RJ45 connection for connection to a computer device or other network device such as a network hub. For wireless transmission it may comprise a wireless interface such as a WLAN interface or a cellular network interface, for example for transmission of data over a GSM or 3G cellular network. The connection station 10 may also comprise combinations of one or more of the above, for example, it may comprise a USB interface, a WLAN interface and a cellular network interface. The interface may also be used to update the application software on the control module 46 of the connection station 10.

In the example of a wired interface, the connection station 10 can be connected to a computer device and data transmitted to the server system 8 over a communication network comprising the internet via the computer device.

In the example of a wireless interface which is a WLAN interface the connection station 10 can be connected to a computer device for example via a wireless network hub and data transmitted to the server system 8 over a communication network comprising the internet via the computer device.

Referring to FIG. 1, in the example of a wireless interface which is a cellular network interface, the connection station 10 connects over a telecommunication network 50. The telecommunication network 50 comprises a wireless telecommunication transfer network (WTT) 52 and the internet 54. The WTT network 52 comprises a service provider 56, for example Vodaphone™, and a general packet radio service (GPRS) server 58. Data can be transmitted over the WTT network 52 and internet 54 to the server system 8 via the GPRS server 58. In this example the connection station 10 can comprise a subscriber identification module (SIM) 60, as shown in FIG. 3, to enable the connection station be identified and authenticated on the WTT network 52 by the service provider 56.

The server system 8 comprises a database to store the medical data 4, 48. In the example wherein the medical data 48 is encrypted by means of the cryptographic algorithm of the connection station 10, the medical data may be stored in encrypted of decrypted formats. For example, it may be stored encrypted together with an associated decryption algorithm, such as a private key. Alternatively, it may be decrypted by a decryption algorithm of the server system 8 and stored in a decrypted format.

The connection station 10 further comprises a lid which is movably connected to the body 14 such that it is movable between a first position and a second position. In the first position the lid prevents the second portion of the docking interface 94 of the medical device 6 from docking with the first portion 24 of the docking interface of the connection station 10. In the second position the second portion of the docking interface is operable to dock with the first portion of the docking interface.

The lid can be movably connected to the body in a variety of manners, for example it may be: slideably connected by means of a channel and corresponding guide; flexibly connected by means of a flexible connection achieved by an elastic member; rotateably connected by means of a protrusion co-axial a sleeve; pivotally connected.

A connection and subsequent data session between the connection station and server may be initiated by the control unit of the signal processing circuit upon receiving a signal from a connection initiation unit. The connection station may comprise an actuator mounted to the housing which is depressed to effect initiation of the connection. The actuator may be manually actuated by the user, for example, it comprises a button arranged on the housing. The actuator may alternatively be automatically activated, for example, it comprises a button which is depressed by the medical device during docking with the connection station. The connection initiation unit may alternately comprise a light sensing means: such as a light sensitive diode exposed to different intensity light during docking, or a magnetic sensing means: such as a reed switch or other device which is operated by a magnet during docking.

In the example shown in FIGS. 2 and 3 the connection initiation unit comprises a lid and lid movement sensing unit, which are configured to initiate the connection during movement of the lid as is described in more detail below. It will however be appreciated that the connection station may optionally comprise a lid.

The lid 62 is pivotally connected to the body 14. The lid 62 comprises a cover portion 64, for covering the docking interface 24 and hinge portion 66 for the pivoted connection. The hinge portion 66 comprises a sleeve 68 through which a pivot axle 70 extends. The pivot axle 70 comprises an actuation cam portion 72, the operation of which will be discussed in more detail below. The pivot axle 70 is arranged to further extend into hubs 74 of the top wall 22 of the housing 16. The pivot axle 70 rotates with the lid 62 in the hubs 74 such that pivoting of the lid actuates the actuation cam portion 72. It will be appreciated that other suitable pivoted attachments for the lid may be derived, for example the pivot axle can be integrated into the body or lid and inserted into corresponding hubs in the other of the body or lid. Moreover the actuation cam portion may be integrated with the sleeve. FIG. 2a shows the lid 62 in the first position; FIG. 2b shows the lid 62 in the second position; whereas FIG. 2c shows the lid 62 in the second position with medical device 6 docked with the connection station 10.

The lid 62 may be biased into the first position by means of a biasing member. In the example of the pivoted attachment shown in FIGS. 2 and 3 the biasing member may comprise a torsion spring coiled around the pivot axle and abutting at an end the lid and at another end the body.

The connection station 10 further comprises a lid movement sensing unit which is configured to sense movement of the lid between the first position and the second position and to thereby provide a signal to the control unit 38 of the signal processing circuit 36. The control unit 38 is configured to receive the signal to initiate the connection to the server system 8 (including connection to any aforementioned intermediate device such as the GPRS server or a computer device and hub).

The lid movement sensing unit may comprise a variety of configurations, for example: it may comprise a light sensing unit such as a light sensitive diode exposed to different intensity light by movement of the lid between the first and second position; it may comprise a magnetic field sensing unit, such as reed switch or other device which can be operated by a magnet by movement of the lid between the first and second position; it may comprise a mechanically actuated unit, such as a switch unit which is actuated by an actuation member as the lid is moved between the first and second position.

Figure 5:
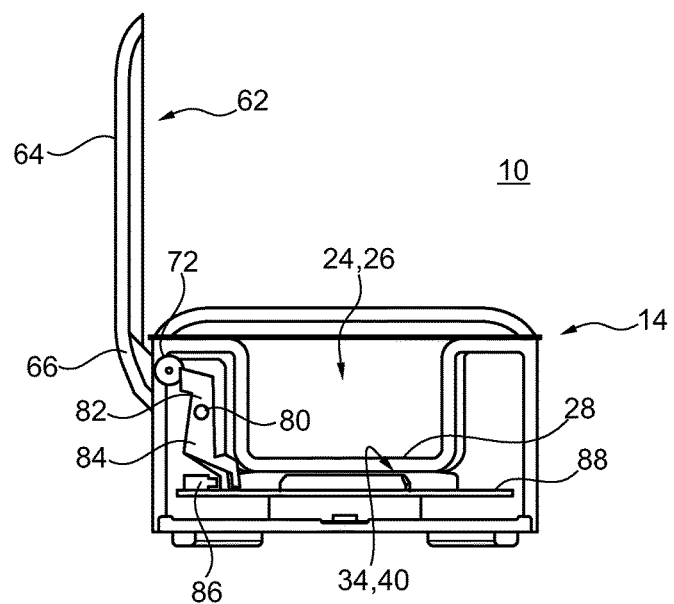
FIG. 5 is a side cross-sectional view of the connection station of FIG. 1.

In the example shown in FIGS. 3 and 5, wherein the lid is pivotally connected to the body, the lid movement sensing unit 76 is mechanically actuated. An actuation member 78 in the form of a lever is pivotally supported by a pivot 80 to define on opposed sides of the pivot 80: a first portion 82, having an actuation cam 62 engaging end; and second portion 84 having a switch unit engaging end. The first portion 82 engages the actuation cam 72, discussed above, such that the actuation member 78 is actuated by the cam 72 as the lid is moved between the first and second position. Actuation of the actuation member causes the second portion 84 to actuate a switch unit 86. The actuation member 78 comprises a biasing member biasing it into contact with the actuation cam 72. In the example the biasing member is a torsion spring 98 coiled around the pivot axle 70 and abutting at an end of the actuation member 78 and at another end of the body 14.

The switch unit 86 is electrically connected to the control unit 38 of the signal processing circuit 36 such that a signal from the switch unit 86 can be received by the control unit. In this example the switch unit is arranged such that it is actuated by means of a pressing force, however, it may be alternatively arranged such that it is actuated by the removal of a pressing force, for instance by arranging it on the other side of the second portion 84 of the actuation member 78. Moreover, other mechanically actuated units may be used, for example: the actuation cam of the lid may directly actuate the switch unit without an actuation member; the switch unit may be actuated by the first portion of the actuation unit, thus obviating the need for the second portion of the actuation unit.

The signal processing circuit 36 may further comprise a circuit board 88 to which various aforementioned components may be mounted. In the example of FIG. 3, the circuit board 88 has mounted thereto the control unit 38, memory unit 44, communication interfaces 40 and 42 and switch unit 86. The infrared transceiver of the medical device communication interface 40 is arranged on the circuit board 88 such that it is below the transmissive window 34 for transmission of data therethrough. The switch unit 86 of the lid movement sensing unit is conveniently supported by on the circuit board for actuation by the actuation member 78. In the example the circuit board comprises mounted thereto a SIM card connector 90 for receiving the SIM card 72 from the SIM card holder 32 and a cell phone network connection chip.

In this way the various electronic hardware components can be conveniently pre-assembled on the circuit board 88 prior to assembly of the circuit board within the housing 16 of the body 14. The circuit board may be arranged within the housing and secured to the housing by various means. In this example the circuit board is planar and is arranged parallel to the base 18. The circuit board is secured to the base 18 and housing 16 by fixing means 96, which herein comprises four bolts inserted vertically through the base and into the housing 16.

The signal processing circuit 36 may further comprise a status indicating unit to indicate a status of the connection station. For example, the status may be one of the following: transmitting data status; completed data transmission status; start-up status; error status. The status indicating unit may be connected to and controlled by the control unit 38. The status indicating unit 92 shown in FIG. 3 comprises a one or more light indication means, such as an LED, which are operable to emit one or a range of wavelengths of light depending on a status.

The control unit of the signal processing circuit may be configured to terminate the connection to the server system upon receiving a further signal from the connection initiation unit. In the example comprising a lid and a lid movement sensing unit, the connection is terminated upon movement of the lid from the second position to the first position, for example in response to the control unit receiving a further signal from the lid movement sensing unit. The control unit may be configured to terminate the connection to the server system after a predetermined period of time. The predetermined period of time may, for example, be the typical time for transfer of the medical data to the server system.

The signal processing circuit 36 may be configured notify a user, for example using the status indicating unit, when a data transfer session is required. The medical device may alternatively or additionally be configured to operate in this manner. The frequency of the data sessions may be specified by the HCP or via a specific request sent by the HCP from the computer device 12 via the server system 8 to the connection station 10.

A second embodiment of a medical system for remotely transferring medical data from a medical device to a remote server system will now be described. In this embodiment the medical device is a drug delivery device and transfers the medical data directly to the server system thus obviating the need for the connection station of the first embodiment. The drug delivery device of this embodiment comprises the medical device of the first embodiment, but with the addition of various components that are present in the connection station of the first embodiment as will now be described.

The drug delivery device may be adapted for subcutaneous delivery of a medicament or may be adapted for delivery by other means, for example, as an aerosol via an inhaler or orally.

The drug delivery device comprises a signal processing circuit to acquire, store and transmit the medical data via a server communication interface. The signal processing circuit may be idealised as consisting of a: control unit; medical data acquisition unit; and memory unit. The medical data acquisition unit is configured to acquire the medical data, and may for example comprise a sensor for sensing an amount of medicament dispensed or other hardware interface. The control unit is configured to process and store the medical data on the memory unit. The memory unit may consist of a non-volatile memory, such as flash memory. The control unit is further configured to connect with and obtain a data session with a server system via the server communication interface, and to thereby transfer the medical data to the server system.

The medical device may further comprise a user interface, such as a display means for display of the medical data and a user input device comprising selection keys for entry of medical data and/or operation of the medical device. The control unit may be configured to receive the signal from the user interface unit to initiate the connection to the server system. Alternatively or in addition, the control unit control unit may be configured to initiate the connection to the server system at a predetermined time.

The medical device may further comprise a clock module to synchronise the medical data for providing time and date related medical data.

The server communication interface comprises a cellular network interface, as described in the above. The medical device comprises may also comprise other communication interfaces which are also described in the above.

The signal processing circuit may further comprise a control module having a cryptographic algorithm as discussed for the first embodiment. The control module can therefore be configured to encrypt the acquired medical data, and to transfer the encrypted medical data to the server system.

LIST OF REFERENCES

2 Drug administration system
4 Medical data
   48 Encrypted medical data
6 Medical device (drug delivery device)
   Signal processing circuit
      Control unit
      Memory unit
      Medical data acquisition unit
   Connection station communication interface
   User Interface
94 Second portion of docking interface
8 Server system
10 Medical device connection station
   14 Body
      16 Housing
         18 Base
         20 Side wall
         22 Top wall
         32 SIM card holder
         96 Fixing means
      24 First portion of docking interface
         26 Docking interface cavity
         28 Bottom wall
         34 Transmissive window
         30 Side wall
   62 Lid
      64 Cover portion
      66 Hinge portion
         68 Sleeve
         70 Pivot Axle
         72 Actuation cam portion
         74 Hub
   76 Lid movement sensing unit
      78 Actuation member
         80 Pivot
         98 Biasing member
         82 First portion
            Actuation cam engaging end
         84 Second portion
            Switch engaging end
      86 Switch unit
   36 Signal processing circuit
      38 Control unit
   40 Medical device communication interface
      Near field wireless transceiver
      Infrared transceiver
   42 Server communication interface
      60 SIM card
      90 SIM card connector
      Cell phone network connection chip
   44 Memory unit
   46 Control module
   88 Circuit board
   92 Status indicating unit
12 Computer device
50 Telecommunications network
   52 WTT network (wireless telecommunications transfer network)
   56 Service provider
   58 GPRS server (General packet radio service server)
   54 Internet

The invention claimed is:

1. A medical device connection station, comprising a body having a first portion of a docking interface to dock with a corresponding second portion of a docking interface of a medical device, a control unit, comprising a processor coupled to a memory, controlling a medical device communication interface for communication with a docked medical device and controlling a server communication interface, wherein the control unit is configured to acquire medical data from a docked medical device via the medical device communication interface and is further configured to connect with and obtain a data session with a server system via the server communication interface, and to thereby transfer the medical data to the server system, wherein the medical device connection station further comprises a lid connected to the body and movable between a first and second position, wherein in the first position the lid prevents the first portion of the docking interface from docking with the corresponding second portion of the docking interface of the medical device, and wherein in the second position the first portion of the docking interface is operable to dock with the corresponding second portion of the docking interface, wherein the medical device connection station further comprises a lid movement sensing unit which is configured to sense movement of the lid between the first position and the second position and to thereby provide a signal to the control unit, the control unit configured to receive the signal to initiate the connection to the server system and wherein the lid movement sensing unit is configured to sense movement of the lid from the second position to the first position and to thereby provide a further signal to the control unit, the control unit configured to receive the further signal to terminate the connection to the server system, wherein the medical device connection system further comprises a control module having a cryptographic algorithm, the control module configured to encrypt the received medical data, the control unit configured to transfer the encrypted medical data to the server system.

2. The connection station of claim 1, wherein the lid movement sensing unit is mechanically actuated and comprise a switch unit and an actuation member, the actuation member configured to engage with and actuate the switch unit as the lid is moved between the first position and the second position, the switch unit configured to provide the signal.

3. The connection station of claim 2, wherein the switch unit, the control unit, the medical device communication interface and the server communication interface are mounted on a circuit board, the circuit board arranged adjacent to a base of the body and distal from the lid.

4. The connection station of claim 1, wherein the lid is pivotally connected to the body.

5. The connection station of claim 1, wherein the lid movement sensing unit comprises an actuation cam operable to pivot with the lid to actuate an actuation member, the actuation member being pivotally connected to the body.

6. The connection station of claim 1, wherein the lid and the body are configured such that the lid covers the first portion of the docking interface when in the first position.

7. The connection station of claim 1, wherein the server communication interface comprises a cellular network interface including a SIM card connector.

8. The connection station of claim 1, wherein the medical device communication interface comprises an infra-red interface.

9. The connection station of claim 8, wherein the infra-red interface is operable to receive the medical data through a transmissive window in a bottom wall of a docking interface cavity.

10. The connection station of claim 1, wherein the server communication interface comprises wired network interface.

11. The connection station of claim 1, wherein the server communication interface comprises wireless local area network (WLAN) network interface.

12. The connection station of claim 1, wherein the control unit is configured to terminate the connection to the server system after a predetermined period of time.

13. The connection station of claim 1, wherein the medical device is a drug delivery device.

14. The connection station of claim 1, wherein the medical data is related to a dosage regimen of a medicament.

15. A system to transfer medical data from a medical device to a server system comprising: a medical device operable to acquire medical data, a server system and a medical device connection station according to claim 1.

16. The system of claim 15 further comprising a remote computer device configured to remotely access the medical data of the server system over the internet.

17. The method of transferring medical data from a medical device to a server system using a medical device connection station of claim 1, the method comprising:

a. acquiring medical data on the medical device;
b. connecting the medical device connection station to the server system by moving the lid from the first position to the second position;
c. docking the medical device with the medical device connection station by connecting the first and second portions of the docking interface;
d. transferring the medical data from the medical device to the medical device connection station via a communication interface of the medical device and the medical device communication interface of the medical device connection station;
e. transferring the medical data from the medical device connection station to the server system via the server communication interface of the medical device connection station; and
f. encrypting the transferred medical data on the medical device connection station by means of a cryptographic algorithm of a control module and transferring the encrypted medical data to the server system.

18. The method according to claim 17 further comprising storing the transferred medical data on a database of the server system.

19. The method according to claim 17 further comprising remotely accessing the medical data of the server system over the internet using a computer device.

20. A method of transferring medical data from a medical device to a server system using a medical device connection station of claim 1, the method comprising:

a. acquiring medical data on the medical device;
b. connecting the medical device connection station to the server system;
c. docking the medical device with the medical device connection station by connecting the first and second portions of the docking interface;
d. transferring the medical data from the medical device to the medical device connection station via a communication interface of the medical device and the medical device communication interface of the medical device connection station; and
e. transferring the medical data from the medical device connection station to the server system via the server communication interface of the medical device connection station.

* * * * *